(12) United States Patent
Harrison et al.

(10) Patent No.: US 12,087,146 B2
(45) Date of Patent: Sep. 10, 2024

(54) REDUNDANT GAS DETECTION SYSTEM

(71) Applicant: UT-Battelle, LLC, Oak Ridge, TN (US)

(72) Inventors: Matthew S. Harrison, Oak Ridge, TN (US); Anthony D. McBee, Oak Ridge, TN (US); Darren D. Loposser, Oak Ridge, TN (US); Michael E. Bowling, Oak Ridge, TN (US); Nikolas J. Smith, Oak Ridge, TN (US)

(73) Assignee: UT-BATTELLE, LLC, Oak Ridge, TN (US)

( * ) Notice: Subject to any disclaimer, the term of this patent is extended or adjusted under 35 U.S.C. 154(b) by 28 days.

(21) Appl. No.: 17/960,886

(22) Filed: Oct. 6, 2022

(65) Prior Publication Data
US 2023/0117506 A1    Apr. 20, 2023

Related U.S. Application Data

(60) Provisional application No. 63/256,707, filed on Oct. 18, 2021.

(51) Int. Cl.
| | |
|---|---|
| *G08B 21/12* | (2006.01) |
| *G01N 33/00* | (2006.01) |
| *G08B 21/14* | (2006.01) |
| *G08B 29/14* | (2006.01) |

(52) U.S. Cl.
CPC ......... *G08B 21/14* (2013.01); *G01N 33/0031* (2013.01); *G08B 29/14* (2013.01)

(58) Field of Classification Search
CPC ..... G08B 21/14; G08B 29/14; G01N 33/0031
See application file for complete search history.

(56) References Cited

U.S. PATENT DOCUMENTS

| | | | | |
|---|---|---|---|---|
| 5,879,631 | A * | 3/1999 | Wewers | G01N 33/0014 422/83 |
| 5,910,765 | A * | 6/1999 | Slemon | G01D 1/00 340/517 |
| 11,045,800 | B1 * | 6/2021 | Kaplan | G01N 33/0006 |
| 2004/0216514 | A1 | 11/2004 | Nunnally et al. | |

(Continued)

FOREIGN PATENT DOCUMENTS

WO    WO 2015053793    * 10/2013    ........... G01N 21/783

*Primary Examiner* — Hongmin Fan
(74) *Attorney, Agent, or Firm* — WARNER NORCROSS + JUDD LLP

(57) ABSTRACT

A system for redundantly detecting a gas is provided. The system includes first and second series-connected gas sensors and a signaling module. If both gas sensors are functioning normally, the signaling module provides an alert when both gas sensors detect a predetermined gas concentration. If however any one of the gas sensors is experiencing a fault condition, the faulty gas sensor's alarm is shunted by operation of a fault relay, and the signaling module provides an alert when the non-faulty gas sensor detects a predetermined gas concentration. If both gas sensors are experiencing a fault condition, both gas sensors' alarms are shunted by fault relays, and an audible and/or visual alert is generated by the signaling module. Embodiments of the present invention are well suited for industrial facilities, manufacturing facilities, research and development laboratories, and other locations where unsafe gas concentrations may become present.

20 Claims, 4 Drawing Sheets

(56) References Cited

U.S. PATENT DOCUMENTS

2012/0081699 A1\* 4/2012 Ford ................. E21B 47/114
 356/128
2020/0383172 A1\* 12/2020 McCracken ......... H04W 88/06

\* cited by examiner

| INPUTS | | | | OUTPUTS | | |
|---|---|---|---|---|---|---|
| ODH1 | ODH2 | FAULT1 | FAULT2 | LIGHT/SIREN | SENSOR 1 FAILURE | SENSOR 2 FAILURE |
| T | F | F | F | F | F | F |
| F | T | F | F | F | F | F |
| T | T | F | F | T | F | F |
| F | F | T | F | F | T | F |
| F | F | F | T | F | F | T |
| T | F | F | T | T | F | F |
| F | T | T | F | T | F | F |
| F | F | T | T | T | F | F |

FIG. 3

REDUNDANT GAS DETECTION SYSTEM

CROSS-REFERENCE TO RELATED APPLICATIONS

This application claims the benefit of U.S. Provisional Application 63/256,707, filed Oct. 18, 2021, the disclosure of which is incorporated by reference in its entirety.

STATEMENT REGARDING FEDERALLY SPONSORED RESEARCH AND DEVELOPMENT

This invention was made with government support under Contract No. DE-AC05-000R22725 awarded by the U.S. Department of Energy. The government has certain rights in the invention.

FIELD OF THE INVENTION

The present invention relates to systems for detecting an alarm condition related to gas concentration levels in ambient air.

BACKGROUND OF THE INVENTION

Many workplaces, for example, research laboratories and industrial facilities, can require atmospheric monitoring to ensure oxygen concentrations are kept at acceptable levels. According to workplace standards from the Occupational Safety and Health Administration, humans begin to suffer adverse health effects in oxygen-deficient atmospheres when oxygen concentrations drop below 19.5%. Similarly, oxygen concentrations of more than 22% can be hazardous, primarily due to the increased risk of fire in an oxygen-rich environment.

Existing oxygen concentration sensors include electrochemical sensors, zirconium sensors, and ultrasonic sensors. These sensors provide an electrical output proportional to the oxygen concentration in ambient air. While widely utilized, oxygen concentration sensors nearing the end of their lifespan will eventually fail, resulting in an alarm state. The resulting alarm can prompt an unnecessary evacuation and cause burdensome downtime for laboratory and manufacturing operations. Routine false alarms may also result in the occupants disabling the oxygen concentration sensors to prevent false alarms, presenting workplace safety concerns and violations.

Accordingly, there remains a continued need for an improved system that detects unsafe gas concentration levels while minimizing false alarms. In addition, there remains a continued need for an improved system that provides for the redundant detection of gas concentration levels in case a system fault should arise.

SUMMARY OF THE INVENTION

A system for redundantly monitoring or detecting a gas is provided. The system includes first and second series-connected gas sensors and a signaling module. If both gas sensors are functioning normally, the signaling module provides an alert when both gas sensors detect a predetermined gas concentration. If however any one of the gas sensors are experiencing a fault condition, the faulty gas sensor is shunted by operation of a fault relay, and the signaling module provides an alert when the non-faulty gas sensor detects a predetermined gas concentration. If both gas sensors are experiencing a fault condition, both gas sensors are shunted by fault relays, and an audible and/or visual alert is generated by the signaling module. Embodiments of the present invention are well suited for industrial facilities, manufacturing facilities, research and development laboratories, and other locations where unsafe gas concentrations may become present.

In one embodiment, each gas sensor includes a detector switch and a fault relay. Each detector switch is a normally-open electrical switch that closes based on a measured gas concentration relative to a predetermined gas concentration. For example, the detector switch can close in response to a measured oxygen concentration being less than a predetermined minimum oxygen concentration. Each fault relay is connected in parallel with a detector switch and shunts the corresponding detector switch in response to a fault condition for the corresponding gas sensor.

In another embodiment, the signaling module is configured to generated a visual alert and/or an audible alert. For example, the signaling module can include a light beacon and an annunciator supported on a portable housing. The annunciator can generate an audible alert to indicate the appropriate response action based on the measured gas concentration. In the case of a faulty sensor, the annunciator can also identify the faulty sensor and the nature of the fault.

While primarily described above as detecting an oxygen deficiency in ambient air, other gases can be measured in other embodiments. For example, the system can monitor for unsafe levels of hydrogen, nitrous oxide, carbon dioxide, argon, and/or helium. In addition, the system of the present invention can initiate a gas shut-off and/or ventilation system depending on facility requirements. As noted above, the system of the present invention is well suited for workplaces where unsafe gas concentrations may become present, including industrial facilities, manufacturing facilities, research and development laboratories, and other workplaces.

These and other features of the invention will be more fully understood and appreciated by reference to the description of the current embodiments.

Before embodiments of the invention are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. In addition, phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

BRIEF DESCRIPTION OF THE DRAWINGS

FIG. 3 is a logic table for use with the system shown in FIG. 1.

DETAILED DESCRIPTION OF THE CURRENT EMBODIMENTS

Figure 1:
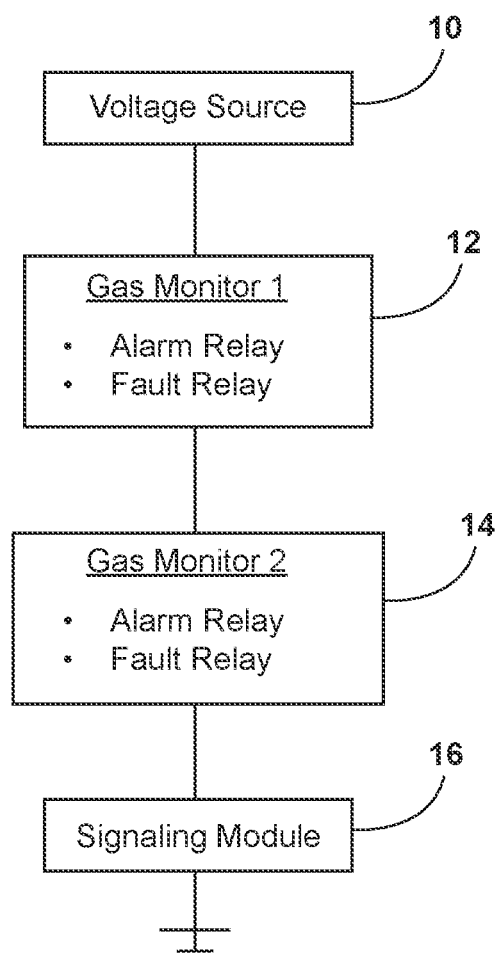
FIG. 1 is a system block diagram in accordance with one embodiment.

Referring to FIG. 1, a high-level block diagram of a system for redundantly detecting a gas concentration is illustrated. The system generally includes a voltage source 10, two series-connected gas sensors 12, 14, and a signaling module 16. If both gas sensors 12, 14 are functioning normally, the signaling module 16 provides an alert when both gas sensors 12, 14 detect a predetermined gas concentration. If however any one of the gas sensors 12, 14 is not functioning normally, the faulty gas sensor is bypassed by operation of a fault relay for that gas sensor, and the signaling module 16 provides an alert when the non-faulty gas sensor detects a predetermined gas concentration. The signaling module 16 can generate an audible alarm and/or a visible alarm, and the system can initiate a gas-shut off and/or ventilation system depending on the particular gas concentration being monitored. As used herein, the term "gas sensor" means any device which detects, monitors or measures the presence or concentration of a gas or a vapor. The gas sensors used in the present embodiment are described below as monitoring an oxygen concentration in ambient air, however other gases can be detected, monitored or measured in other embodiments, including for example hydrogen, nitrous oxide, carbon dioxide, argon, and helium.

Figure 2:
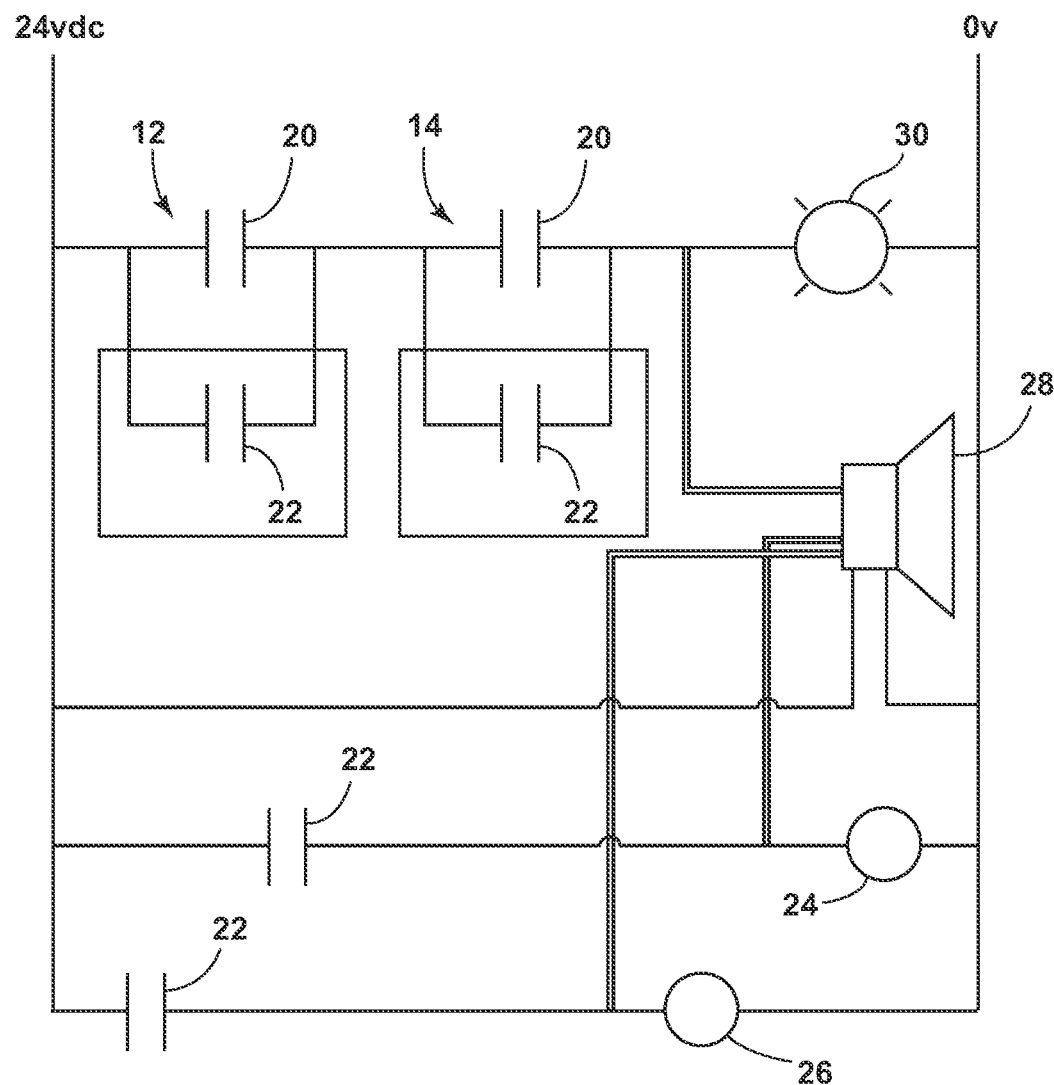
FIG. 2 is a circuit diagram of one implementation of the system of FIG. 1.

As more specifically shown in FIG. 2, the system includes first and second oxygen concentration sensors 12, 14 that are series connected between a 24V supply voltage and ground. The oxygen concentration sensors 12, 14 can detect the oxygen concentration according to any suitable method and can comprise electrochemical sensors, zirconium sensors, or ultrasonic sensors, by non-limiting example. An example electrochemical sensor includes the GD-70D gas detector by RKI Instruments, however other sensors can be used in other embodiments. The oxygen concentration sensors 12, 14 are identical in the illustrated embodiment, but can be dissimilar in other embodiments. Each such oxygen concentration sensor 12, 14 includes a normally-open detector switch 20 that closes when the oxygen concentration is less than a predetermined threshold. For example, the detector switch 20 can close when the oxygen concentration in ambient air is equal to or below 19.5%. Other thresholds can be used in other embodiments, depending on the gas being measured. Rather than detecting a minimum gas concentration, for example, the normally-open detector switch 20 can close in response to the detected concentration being greater than a predetermined threshold, particularly when hazardous or combustible gases are monitored.

As also shown in FIG. 2, each detector switch 20 is parallel connected with a fault relay 22. The fault relay 22 includes a 700-HLT1Z24 electromechanical relay by Allen-Bradley PLC in the illustrated embodiment, however essentially any relay switch can be used in other embodiments. The fault relay 22 closes in response to a fault condition being detected at the corresponding gas concentration sensor 12, 14. That is, each gas sensor 12, 14 includes a self-diagnostic function that provides an output in the case of a sensor fault. This output is coupled to the fault relay 22 and causes the fault relay 22 to close, thereby bypassing the detector switch 20 for the faulty gas sensor. Simultaneously, the faulty gas sensor generates an error code to indicate that servicing or replacement of the gas sensor is needed. The detected fault can cause a corresponding LED 24, 26 to illuminate and can cause a pre-recorded MP3 file to play over an annunciator 28, for example a BSV Voice Annunciator by PATLITE Corporation. The system can continue to operate even while the fault is present, which is made possible by the non-faulty gas concentration sensor.

FIG. 3 illustrates a truth table for one exemplary embodiment. The inputs include the first detector switch (ODH1), the second detector switch (ODH2), the first fault relay (FAULT1), and the second fault relay (FAULT2). The outputs include a light and/or siren as generated by the signaling module 16, a first gas sensor error code as generated by the first gas sensor 12, and a second gas sensor error code as generated by the second gas sensor 14. The signaling module 16 generates a visible and/or audible alert if any one of the following conditions are met: (a) two normally-operating gas sensors each detect a predetermined gas concentration; (b) one normally-operating gas sensor detects a predetermined gas concentration while the other gas sensor is experiencing a fault condition; or (c) both gas concentration sensors are experiencing a fault condition. In the illustrated embodiment, the signaling module 16 includes the aforementioned annunciator 28 and a beacon light 30, for example the MS86L-B02-B beacon light from Menics Signal Technology. However, the signaling module 16 can include essentially any audible and/or visual alert as desired. The annunciator can clearly state the nature of the hazard and can provide instructions to personnel exposed to this hazard. While it is generally desired that the signaling module 16 provides an audible alert and a visual alert, in some embodiments only a visual alert is provided, while in other embodiments only an audible alert is provided.

Figure 4:
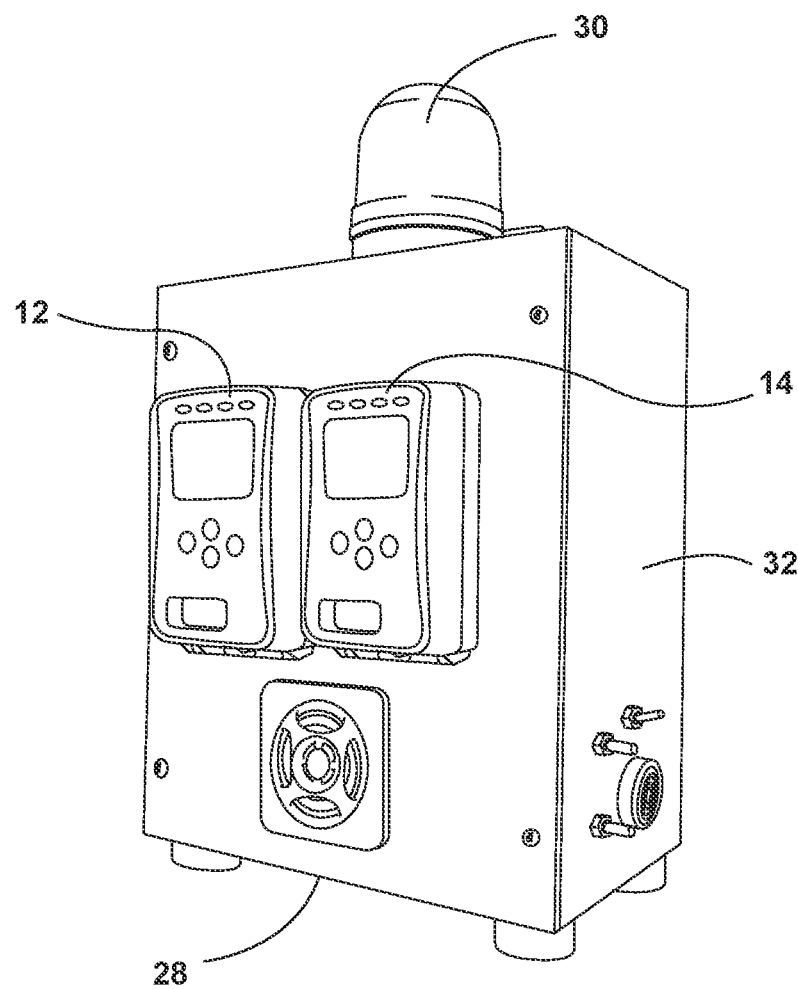
FIG. 4 illustrates a portable unit for monitoring gas concentrations.

One example of the system of the present invention is illustrated in FIG. 4. In this example, the system comprises a table-top unit having two oxygen concentration sensors 12, 14, an annunciator 28, and a beacon light 30. The table-top unit includes a rigid outer housing 30 that functions as a mounting platform for all associated hardware. Each oxygen concentration sensor 12 is readily accessible for servicing and/or replacement in the case of a fault condition. While illustrated as a table-top unit, in other embodiments the system is wall mounted. In instances where an excessive concentration of a hazardous gas is detected, the system can initiate a gas-shut off and/or ventilation system depending on the particular gas concentration being monitored, optionally over a wireless connection, for example a Bluetooth or WiFi connection.

In operation, and after the system is powered on, each gas concentration sensor 12, 14 can be initialized and its status can be displayed. If either gas concentration sensor 12, 14 detects a fault as part of its self-diagnostic functionality, that gas concentration sensor provides an output to a corresponding fault relay. The fault relay bypasses the faulty gas concentration sensor and generates an audible alarm via the annunciator 28 to indicate a fault exists while retaining gas monitoring functionality via the working sensor. The non-faulty gas concentration sensor will continue to monitor gas concentrations and can generate an alarm condition without requiring agreement with the faulty gas concentration sensor. If at any time a fault condition is detected in the working sensor, the corresponding fault relay bypasses the faulty gas concentration sensor's alarm output and the signaling module 16 generates an audible alarm via the annunciator 28 and the beacon light 30.

While described above in connection with fault relays, in another embodiment each gas concentration sensor 12, 14 provides an output to a processor for digital control of the signaling module 16 in accordance with the truth table of FIG. 3. In this embodiment, the processor includes digital logic that requires agreement of two non-faulty gas sensor in accordance with the truth table of FIG. 3 before an alarm can be generated. If one gas sensor is experiencing a fault condition, the processor initiates an alarm when the non-faulty gas sensor detects a predetermined gas concentration. The annunciator can clearly state the nature of the hazard, e.g., an oxygen deficiency, and can provide instructions to personnel exposed to this hazard. If both gas sensors are experiencing a fault condition, the processor initiates an alarm at the signaling module 16, which then generates an audible alert indicating that gas concentrations are no longer reliably monitored, along with instructions for personnel in the immediate vicinity.

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

The invention claimed is:

1. A system for redundantly detecting or monitoring a gas, the system comprising:
a signaling module configured to issue audio or visual signals; and
a first gas sensor and a second gas sensor connected in series with each other and the signaling module such that each of the first gas sensor, the second gas sensor, and the signaling module are series connected between a supply voltage and a ground, wherein each of the first and second gas sensors is configured to detect presence of the gas and comprises:
a respective detector switch configured to allow a current through the gas sensor when the gas presence detected by the gas sensor meets a predetermined target, wherein the current causes the signaling module to issue a warning signal, and
a respective fault relay configured to determine a fault of the gas sensor, and upon determination of the fault, shunt the gas sensor and cause the signaling module to issue a fault signal associated with the gas sensor,
wherein the respective detector switch is a normally-open detector switch, such that the current flows through the respective detector switch in response to activation of the respective detector switch and alternatively the current bypasses the respective detector switch in response to activation of the respective fault relay.

2. The system of claim 1, wherein the signaling module is configured to issue, as the warning signal, an audio signal identifying a hazard when the gas presence reaches a predetermined concentration in an ambient gas mixture.

3. The system of claim 1, wherein the signaling module is configured to issue, as the warning signal, an audio signal indicating deficiency of the gas when the gas presence is under a predetermined concentration in an ambient gas mixture.

4. The system of claim 1, wherein the signaling module is configured to issue, as the warning signal, a visual signal along with the audio signal.

5. The system of claim 1, wherein the signaling module is configured to issue, as part of the warning signal, appropriate response actions based on the detected gas presence.

6. The system of claim 1, wherein the signaling module is configured to issue, as the fault signal, an audio signal and/or a visual signal identifying the faulty gas sensor.

7. The system of claim 6, wherein the issued audio or visual signal indicates a type of the determined fault.

8. The system of claim 1, wherein the first and second gas sensors are oxygen concentration sensors, and wherein the predetermined target is a predetermined minimum oxygen concentration or a predetermined maximum oxygen concentration.

9. The system of claim 8, wherein each respective detector switch changes state in response to a measured oxygen concentration being less than or greater than the predetermined minimum oxygen concentration.

10. The system of claim 1, wherein the signaling module and the first and second gas sensors are supportably received within a housing.

11. A system for redundantly detecting a gas comprising:
first and second gas sensors each being adapted to measure a gas concentration in ambient air, wherein the first gas sensor includes a first gas detector switch and wherein the second gas sensor includes a second gas detector switch, wherein each of the first and second gas detector switches include an electrical switch that changes from a first state to a second state based on a measured gas concentration relative to a predetermined gas concentration;
a first fault relay connected in parallel with the first gas detector switch, and a second fault relay connected in parallel with the second gas detector switch, wherein the first fault relay shunts the first gas detector switch in response to a fault in the first gas sensor, and wherein the second fault relay shunts the second gas detector switch in response to a fault in the second gas sensor; and
a signaling module electrically connected in series with the first gas detector switch and the second gas detector switch, the signaling module being configured to issue an alert in response to:
the first gas detector switch being in the second state in combination with the second gas detector switch being in the second state, the first gas detector switch being in the second state in combination with a fault in the second gas sensor, the second gas detector switch being in the second state in combination with a fault in the first gas sensor, and a fault in the first gas sensor in combination with a fault in the second gas sensor.

12. The system of claim 11, wherein the first and second gas sensors are oxygen concentration sensors, and wherein the predetermined gas concentration is a predetermined minimum oxygen concentration or a predetermined maximum oxygen concentration in ambient air.

13. The system of claim 12, wherein each of the first and second gas detector switches changes from the first state to the second state in response to the measured oxygen concentration being less than the predetermined minimum oxygen concentration or greater than the predetermined maximum oxygen concentration.

14. The system of claim 11, wherein the signaling module includes a light beacon and an annunciator.

15. The system of claim 14, wherein the alert includes a visual alert via the light beacon and an audible alert via the annunciator.

16. The system of claim 15, wherein the audible alert announces the gas concentration as being less than the predetermined gas concentration.

17. The system of claim 15, wherein the audible alert announces the gas concentration as being greater than the predetermined gas concentration.

18. The system of claim 14, wherein the annunciator is operable to issue an audible alert in response to a fault in the first gas sensor or a fault in the second gas sensor.

19. The system of claim 14, wherein the alert includes an appropriate response action as broadcast by the annunciator.

20. The system of claim 11, wherein the first and second gas sensors, the first and second fault relays, and the signaling module are supportably received within a housing.

* * * * *